(12) United States Patent (10) Patent No.: US 8,703,139 B2
Hofbauer et al. (45) Date of Patent: Apr. 22, 2014

(54) MONOCLONAL ANTIBODIES AND BINDING FRAGMENTS THEREOF DIRECTED TO THE MELANOCORTIN-4 RECEPTOR AND THEIR USE IN THE TREATMENT OF CACHEXIA AND RELATED CONDITIONS AND DISEASES

(75) Inventors: Karl Hofbauer, Basel (CH); Jean Christophe Peter, Ammerschwihr (FR)

(73) Assignee: Universitaet Basel, Basel (CH)

( * ) Notice: Subject to any disclaimer, the term of this patent is extended or adjusted under 35 U.S.C. 154(b) by 0 days.

(21) Appl. No.: 13/560,638

(22) Filed: Jul. 27, 2012

(65) Prior Publication Data

US 2013/0058941 A1 Mar. 7, 2013

Related U.S. Application Data

(62) Division of application No. 12/811,249, filed as application No. PCT/IB2008/003651 on Dec. 30, 2008, now Pat. No. 8,252,908.

(60) Provisional application No. 61/029,661, filed on Feb. 19, 2008, provisional application No. 61/018,360, filed on Dec. 31, 2007.

(51) Int. Cl.
*A61K 39/395* (2006.01)

(52) U.S. Cl.
USPC ..................................... 424/143.1; 424/141.1

(58) Field of Classification Search
None
See application file for complete search history.

(56) References Cited

U.S. PATENT DOCUMENTS

| | | | |
|---|---|---|---|
| 5,703,220 A | 12/1997 | Yamada et al. | |
| 5,908,609 A | 6/1999 | Lee et al. | |
| 6,573,070 B1 | 6/2003 | MacNeil et al. | |
| 8,008,446 B2 | 8/2011 | Hofbauer et al. | |

FOREIGN PATENT DOCUMENTS

| | | | | |
|---|---|---|---|---|
| EP | 1167386 A | | 1/2002 | |
| KR | 427645 | * | 4/2004 | .............. C07K 7/06 |
| WO | 0027863 A | | 5/2000 | |

OTHER PUBLICATIONS

Li et al. 2012. FASEB J. 26:3969-3979.*
Yu et al. 20111. Science Transl. Med 3:84ra44.*
Lampson et al. 2011. MAbs 3:153-160.*
Peter et al., "Antibodies against the melanocortin-4 receptor act as inverse agonists in vitro and in vivo," in American Journal of Physiology—Regulaty Integrative and Comparative Physiology, vol. 292, No. 6, Jun. 2007, pp. R2151-R2158.
Foster et al., "Melanocortin-4 receptor antagonists as potential therapeutics in the treatment of cachexia," in Current Topics in Medicinal Chemistry, Bentham Science Publishers, Hilversum, NL, vol. 7, No. 11, Jun. 1, 2007, pp. 1131-1136.
Nicholson et al., "Melanocortin-4 receptor activation stimulates hypothalamic brain-derived neurotrophic factor release to regulate food intake body temperature and cardiovascular function," in Journal of Neuroendocrinology, vol. 19, No. 12, Dec. 2007, pp. 974-982.
Hofbauer et al., "Antibodies as pharmacologic tools for studies on the regulation of energy balance," in Nutrition, Elsevier Inc, vol. 24, No. 9, Sep. 1, 2008, pp. 791-797.
Siegel et al., "Recombinant monoclonal antibody technology," in Transfus Clin Biol, vol. 9(1), Jan. 2002, pp. 15-22.

* cited by examiner

*Primary Examiner* — Shulamith H Shafer
(74) *Attorney, Agent, or Firm* — Joyce von Natzmer; Agris & von Natzmer LLP

(57) ABSTRACT

Disclosed are monoclonal antibodies, binding fragments, and derivatives thereof directed to the human melanocortin-4 receptor, as well as pharmaceutical compositions including the same, the therapeutic uses, including methods for treating cachexia and related conditions and diseases, using such monoclonal antibodies, binding fragments, derivatives, and pharmaceutical compositions.

16 Claims, 20 Drawing Sheets

| | |
|---|---|
| 1 | MNSTHHHGMYTSLHLWNRSSHGLHGNASESLGKGHSDGGCYEQLFVSPEVFVTLGVISLL |
| 61 | ENILVIVAIAKNKNLHSPMYFFICSLAVADMLVSVSNGSETIVITLLNSTDTDAQSFTVN |
| 121 | IDNVIDSVICSSLLASICSLLSIAVDRYFTIFYALQYHNIMTVRRVGIIISCIWAACTVS |
| 181 | GVLFIIYSDSSAVITCLITMFFTMLVLMASLYVHMFLMARLHIKRIAVLPGTGTIRQGAN |
| 241 | MKGAITLTILIGVFVVCWAPFFLHLLFYISCPQNPYCVCFMSHFNLYLILIMCNAVIDPL |
| 301 | IYALRSQELRKTFKEIICFYPLGGICELPGRY |

(SEQ ID NO:1)

Fig. 1

(■) specificity of mAb 1E8a for NT4
(●) specificity of mAb 2G2 for NT4
(▼) specificity of mAb 1E8a for NT3

```
1    GAGTTCCAGC TGCAGCAGTC TGGACCTGAG CTGGTGGAGC CTGGCGCTTC
51   AGTGAAGATA TCCTGCAAGG CTTCTGGTTA CTCATTCACT GACTACAACA
101  TGAACTGGGT GAAGCAGAGC AATGGAAAGA GCCTTGAGTG GATTGGAGTA
151  ATTAATCCTA ACTATGGTAC TACTAGCTAC AATCAGAAGT TCAAGGGCAA
201  GGCCACATTG ACTGTAGACC AATCTTCCAG CACAGCCTAC ATGCAGCTCA
251  ACAGCCTGAC ATCTGAGGAC TCTGCAGTCT ATTACTGTGC AAGATTTGAT
301  GGTTACTACG GTTACTACTT TGACTACTGG GGCCAAGGCA CCACTCTCAC AGTC
```
(SEQ ID NO:4)

Fig. 4A

```
1    EFQQSGPELVEPGASVKISCKASGYSFTDYNMNWVKQSNGKSLEWIGVINPNYGTTSYNQ
                              CDRH1                    CDRH2

61   KFKGKATLTVDQSSSTAYMQLNSLTSEDSAVYYCARFDGYYGYYFDYWGQGTTLTV
                                       CDRH3
```
(SEQ ID NO:5)

Fig. 4B

```
1    GACATTGTGA TGACCCAGTC TACATCCTCC CTGTCTGCCT CTCTGGGAGA
51   CAGAGTCACC ATCAGTTCCA GGGCAAGTCA GGACATTAGC AATTATTTAA
101  ACTGGTATCA GCAGAAACCA GATGGAACTG TTAAACTCCT GATCTACTAC
151  ACATCAAGAT TACACTCAGG AGTCCCATCA AGGTTCAGTG GCAGTGGGTC
201  TGGAACAGAT TATTCTCTCA CCATTAGCAA CCTGGAGCAA GAAGATATTG
251  CCACTTACTT TTGCCAACAG GGTAATACGC TTCCGTACAC GTTCGGAGGG
301  GGGACCAAGC TGGAAATAAA A
(SEQ ID NO:6)
```

Fig. 5A

```
1    DIVMTQSTSSLSASLGDRVTISCRASQDISNYLNWYQQKPDGTVKLLIYYTSRLHSGVPS
                           CDRL1                        CDRL2

61   RFSGSGSGTDYSLTISNLEQEDIATYFCQQGNTLPYTFGGGTKLEIK
                                 CDRL3
(SEQ ID NO:7)
```

Fig. 5B

```
  1   CAGATCCAGT TGGTGCAGTC TGGACCTGAG CTGAAGAAGC CTGGAGAGAC
 51   AGTCAAGATC TCCTGCAAGG CTTCTGGGTA TACCTTCACA ACTGCTGGAA
101   TGCAGTGGGT GCAAAAGATG CCAGGAAAGG GTTTTAAGTG GATTGGCTGG
151   ATAAACACCC ACTCTGGAGA GCCAAAATAT GCAGAAGACT TCAAGGGACG
201   GTTTGCCTTC TCTTTGGAAA CCTCTGCCAG CACTGCCTAT TTACAGATAA
251   GCAACCTCAA AAATGAGGAC ACGGCTACGT ATTTCTGTGC GAGGGGGTTA
301   TTACTACGGC TCTGGGGCCA AGGGACTCTG GTCACTGTC
```

(SEQ ID NO:8)

Fig. 6A

```
  1        QIQLVQSGPELKKPGETVKISCKASGYTFTTAGMQWVQKMPGKGFKWIGWINTHSGEPKY
                                 CDRH1                        CDRH2

61       AEDFKGRFAF SLETSASTAY LQISNLKNED TATYFCARGL LLRLWGQGTL VTV
                                                   CDRH3
```

(SEQ ID NO:9)

Fig. 6B (■) mAb 2G2
(▲) PBS (■) mAb 1E8a
(▲) PBS

|  | Parameters | 1E8a (active mAb) | 2G2 (control mAb) |
|---|---|---|---|
|  | Binding (Kd) | $2.3 \times 10^{-9}$ (M) | n.d. |
| Staining | MC4R | + | - |
|  | MC3R | - | - |

Fig. 9

H1: CKASGYSFTDYNMNC
(SEQ ID NO: 10)

H2: CSLEWIGVINPNYGTTSYC
(SEQ ID NO: 11)

H3: CARFDGYYGYYFDYWGQC
(SEQ ID NO: 12)

L1: CRASQDISNYLNWYQC
(SEQ ID NO: 13)

L2: CYTSRLHSGVPSRFSGSC
(SEQ ID NO: 14)

L3: CQQGNTLPYTFGGGC
(SEQ ID NO: 15)

Fig. 18

Variable domain of the heavy chain

```
EFQLQQSGPELVEPGASVKISCKASGYSFTDYN
                              ――――――――――
                                 CDRH1
MNWVKQSNGKSLEWIGVINPNYGTTSYNQKFKG
                      ――――――――――――――――
                             CDRH2
KATLTVDQSSSTAYMQLNSLTSEDSAVYYCARF

DGYYGYYFDYWGQGTTLTV          SEQ ID NO: 16
――――――――――――
   CDRH3
```

Variable domain of the light chain

```
DIVMTQSTSSLSASLGDRVTISCRASQDISNYL
                          ――――――――――――
                              CDRL1
NWYQQKPDGTVKLLIYYTSRLHSGVPSRFSGSG
                ―――――――
                 CDRL2
SGTDYSLTISNLEQEDIATYFCQQGNTLPYTFG
                         ―――――――――――――
                             CDRL3
GGTKLEIK                    SEQ ID NO: 17
```

Fig. 20

MONOCLONAL ANTIBODIES AND BINDING FRAGMENTS THEREOF DIRECTED TO THE MELANOCORTIN-4 RECEPTOR AND THEIR USE IN THE TREATMENT OF CACHEXIA AND RELATED CONDITIONS AND DISEASES

CROSS REFERENCE TO RELATED APPLICATIONS

This is a divisional application of application Ser. No. 12/811,249 filed Dec. 30, 2008, which is incorporated herein by reference in its entirety and which is the U.S. national stage of International application no. PCT/IB2008/003651, filed Dec. 30, 2008 designating the United States and which claims the benefit of provisional Application No. 61/018,360, filed Dec. 31, 2007 and provisional Application No. 61/029,661, filed Feb. 19, 2008.

FIELD OF THE INVENTION

The present invention relates to monoclonal antibodies and binding fragments thereof directed to the human melanocortin-4 receptor and methods for treating cachexia and related conditions and diseases using such monoclonal antibodies and binding fragments, and further relates to pharmaceutical compositions including such monoclonal antibodies and binding fragments as well as therapeutic uses of such compositions.

BACKGROUND OF RELATED TECHNOLOGY

Patients with chronic diseases such as cancer or infections often exhibit decreased or a loss of appetite (anorexia) which over a prolonged period of time leads to cachexia, a condition in which the patient loses fat and skeletal muscle mass and which is often accompanied by inflammatory conditions. Cachexia has been increasingly recognized as an independent risk factor for morbidity and mortality.

Conventional treatment for cachexia includes diet modification, and pharmacotherapy for which a number of drugs may be used, including corticosteroids such as prednisolone, progestational agents such as megestrol acetate and medroxyprogesterone acetate, and serotonin antagonists such as cyproheptadine (see in this regard, for example, Cancer Medicine 6, Table 144-2 "Pharmacologic Treatment of Cancer Cachexia"). However, such treatments are less than ideal as these drugs have known side effects which may be of particular concern in patients exhibiting cachexia as a result of a chronic condition which may be exacerbated by such side effects. As such, there is a continuing need to develop new therapeutics for use in the treatment of cachexia and related conditions.

In this regard, the human melanocortin-4 receptor ("MC4-R"), which is part of a central appetite reducing (anorexigenic) pathway, has been a target of research interest, as patients suffering from such chronic diseases typically exhibit increased cytokine production which activates the MCR4-R, leading to anorexia and eventually cachexia. For example, PCT Patent Application Publication No. 97/47316 discloses drug screening assays for identifying therapeutics useful in treating body weight disorders based on the MC4-R.

MC4-R is a G-protein coupled receptor (GPCR) which has been shown to be expressed primarily in the brain (Gantt et al., 1993, J. Biol. Chem. 268:15174-15179; Mountjoy et al., 1994, Mol. Endo. 8:1298-1308) and is known to play a crucial role in energy balance (Cowley, M A, Eur. J. Pharmacol. 480:3-11, 2003; Elies, R. et al. Eur. J. Biochem. 251:659-666, 1998). The sequences of the MC4-R in various organisms have been reported in the literature. In this regard, see for example European Patent Application No. 1167386 (canine and feline sequences) and U.S. Pat. Nos. 5,703,220 and 6,117, 975 (human sequences).

Non-antibody compounds that affect the activity of the MC4-R have been reported (see in this regard, for example, U.S. Pat. No. 7,169,777, U.S. Patent Publication No. 2004/0082779, European Patent Application No. 1167386 and PCT Publication Nos. WO 01/085930 and 98/10068). Moreover, polyclonal antibodies have been generated against the MC4-R (Peter et al., Am. J. Physiol. Re ug 1. Integr. Comp. Physiol. 292:R2151-R2158, 2007), however monoclonal antibodies against the MC4-R have not been reported.

Accordingly, there exist needs in the art to develop new and improved therapeutic agents for the treatment of cachexia and related conditions, including the development of therapeutic agents, and in particular monoclonal antibodies, that modulate MC4-R activity. It is to these needs that the present invention is directed.

SUMMARY OF THE INVENTION

It is an object of the present invention to provide monoclonal antibodies directed to the melanocortin-4 receptor and portions of the melanocortin-4 receptor, their therapeutic uses, and methods for treating cachexia and related conditions and diseases using such monoclonal antibodies and binding fragments. It is further an object of the present invention to provide pharmaceutical compositions including such monoclonal antibodies and binding fragments, also in combination with additional therapeutic agents, and the therapeutic uses of such compositions.

In this regard, in one embodiment there is provided an isolated monoclonal antibody or binding fragment thereof that binds to the melanocortin-4 receptor or a portion of the melanocortin-4 receptor.

In some embodiments of the present invention, the isolated monoclonal antibody or binding fragment thereof binds to a portion of the melanocortin-4 receptor comprising the amino acid sequence set forth in SEQ ID NO: 2.

In some embodiments of the present invention, the isolated monoclonal antibody or binding fragment thereof comprises the variable domain of the heavy chain of the isolated monoclonal antibody.

In some embodiments of the present invention, the isolated monoclonal antibody or binding fragment thereof comprises the variable domain of the light chain of the isolated monoclonal antibody.

In some embodiments of the present invention, the isolated monoclonal antibody or binding fragment thereof comprises one or more of the amino acid sequences set forth in SEQ ID NO:5, SEQ ID NO:7, and SEQ ID NO:9.

In some embodiments of the present invention, the isolated monoclonal antibody or binding fragment thereof comprises one or more of the amino acid sequences which are encoded by the nucleic acid sequences set forth in SEQ ID NO:4, SEQ ID NO:6, and SEQ ID NO:8.

In some embodiments of the present invention, the isolated monoclonal antibody or binding fragment thereof is an antagonist or a reverse agonist of the melanocortin-4 receptor.

In some embodiments of the present invention, the isolated monoclonal antibody or binding fragment thereof is produced recombinantly.

In some embodiments of the present invention, there is provided a pharmaceutical composition comprising a therapeutically effective amount of an isolated monoclonal antibody or binding fragment thereof according to any of the preceding embodiments.

In some embodiments of the present invention, the pharmaceutical composition further comprises an active therapeutic agent in combination with and different from the isolated monoclonal antibody or binding fragment thereof.

In some embodiments of the present invention, there is provided a method for stimulating the appetite of a mammal comprising administering to a mammal having a reduced appetite an isolated monoclonal antibody or binding fragment thereof according to any of the preceding embodiments.

In some embodiments of the present invention, there is provided a method for treating the symptoms of cachexia in a mammal exhibiting such symptoms by administering to the mammal an isolated monoclonal antibody or binding fragment thereof according to any of the proceeding embodiments.

In some embodiments of the present invention, there is provided an isolated monoclonal antibody or binding fragment thereof comprising one or more of the amino acid sequences set forth in SEQ ID NO:5, SEQ ID NO:7, and SEQ ID NO:9.

In some embodiments of the present invention, there is provided a pharmaceutical composition comprising a therapeutically effective amount of an isolated monoclonal antibody or binding fragment thereof comprising one or more of the amino acid sequences set forth in SEQ ID NO:5 and SEQ ID NO:7 and which is present in the composition in an amount that is therapeutically effective to increase the appetite of a mammal.

In some embodiments of the present invention, the pharmaceutical composition is therapeutically useful for treating the symptoms of cachexia in a patient exhibiting such Symptoms.

In some embodiments of the present invention, there is provided a method for stimulating the appetite of a mammal, comprising administering to a mammal an isolated monoclonal antibody or binding fragment thereof that binds to the melanocortin-4 receptor or a portion of the melanocortin-4 receptor.

In some embodiments of the present invention, the method for stimulating the appetite of a mammal includes administering an isolated monoclonal antibody or binding fragment thereof comprising one or more of the amino acid sequences set forth in SEQ ID NO:5, SEQ ID NO:7, and SEQ ID NO:9.

In some embodiments of the present invention, there is provided a method for treating the symptoms of cachexia in a mammal exhibiting the Symptoms, comprising administering to the mammal a pharmaceutical composition comprising an isolated monoclonal antibody or binding fragment thereof that binds to the melanocortin-4 receptor or a portion of the melanocortin-4 receptor.

In some embodiments of the present invention, the method for treating the symptoms of cachexia comprises administering to the mammal a pharmaceutical composition comprising a monoclonal antibody binding fragment comprising the amino acid sequence set forth in SEQ ID NO:5 which binds to a portion of the melanocortin-4 receptor comprising the amino acid sequence set forth in SEQ ID NO:2.

In some embodiments of the present invention, there is provided the use of a monoclonal antibody or binding fragment thereof that binds to the melanocortin-4 receptor or a portion of the melanocortin-4 receptor for the preparation of a medicament useful for increasing the appetite in a mammal.

In some embodiments of the present invention, there is provided the use of a monoclonal antibody or binding fragment thereof that binds to the melanocortin-4 receptor or a portion of the melanocortin-4 receptor for the preparation of a medicament useful for the treatment of cachexia and related conditions.

In further embodiments the inventive isolated monoclonal antibody or binding fragment thereof comprises a cyclic peptide derived of the variable domain of the light chain of said isolated monoclonal antibody.

In another preferred embodiment the inventive isolated monoclonal antibody or binding fragment thereof comprises a cyclic peptide of the amino acid sequences which are encoded by the nucleic acid sequences set forth in SEQ ID NO:13, SEQ ID NO:14, and SEQ ID NO:15.

In a further embodiment the inventive isolated monoclonal antibody or binding fragment thereof comprises a cyclic peptide derived of the variable domain of the heavy chain of said isolated monoclonal antibody.

In a further preferred embodiment the inventive isolated monoclonal antibody or binding fragment thereof comprises a cyclic peptide of the amino acid sequences which are encoded by the nucleic acid sequences set forth in SEQ ID NO:10, SEQ ID NO:11, and SEQ ID NO:12.

The inventive cyclic peptides referred to above have a molecular weight of about 1.5 kDa. The monoclonal antibody as a whole has a molecular weight of about 150 kDa, whereas the single chain fragments (scFv) of the variable domains of the monoclonal antibody have a molecular weight of about 26 kDa.

Pharmaceutical compositions may comprise said cyclic peptides and/or single chain fragments (scFv) of the variable domains of the monoclonal antibody.

BRIEF DESCRIPTION OF THE DRAWINGS

FIG. 1 shows the amino acid sequence (SEQ ID NO: 1) of the rat melanocortin-4 receptor.

FIGS. 4A and 4B show the nucleic acid sequence (SEQ ID NO:4) and the amino acid sequence (SEQ ID NO:5) of the variable domain of the heavy chain of monoclonal antibody 1E8a, respectively.

FIGS. 5A and 5B show the nucleic acid sequence (SEQ ID NO:6) and the amino acid sequence (SEQ ID NO:7) of the variable domain of the light chain of monoclonal antibody 1E8a, respectively.

FIGS. 6A and 6B show the nucleic acid sequence (SEQ ID NO:8) and the amino acid sequence (SEQ ID NO:9) of monoclonal antibody 2G2, respectively.

FIG. 9 summarizes the immuno-cytochemical staining of cells which express either MCR4 or MCR3 and which were stained with mAb 1E8a or 2G2 (control mAb).

FIG. 18 shows the amino acid sequence of cyclic peptides HI (SEQ ID NO: 10), H2 (SEQ ID NO: 11), H3 (SEQ ID NO: 12), L1 (SEQ ID NO: 13), L2 (SEQ ID NO: 14) and L3 (SEQ ID NO: 15).

FIG. 20 shows the amino acid sequence of the mAb Paratope of mAb 1E8a.

DETAILED DESCRIPTION OF CERTAIN EMBODIMENTS

For a more complete understanding of the present invention, reference is now made to the following description of various illustrative and non-limiting embodiments thereof, taken in conjunction with the accompanying figures which are presented to further describe the invention and assist in its understanding. In the figures of the present invention, the nucleic acid and amino acid sequences are represented in their conventional orientations and by their standard one-letter abbreviations.

The present invention is directed to monoclonal antibodies ("mAbs"), binding fragments and derivatives thereof (collectively referred to herein with respect to the present invention as "monoclonal antibodies" and/or "antibodies") against the human melanocortin-4 receptor ("MC4-R") and their use in the treatment of certain conditions and diseases, including cachexia, and is further directed to pharmaceutical compositions including the inventive mAbs. As discussed herein, the inventive mAbs have been shown in the present invention to be pharmacologically active against the MC4-R, in particular against a short peptide sequence of the constitutive active N-terminal (NT) domain of the MC4-R, and have further been shown to have appetite stimulating effects.

Unless expressly stated otherwise, all terms used herein are given their conventional art recognized definitions which will be readily apparent to those of skill in the art. For example and without limitation, "monoclonal antibodies" include antibodies which are produced by a hybridoma that has been formed by fusing a tumor cell with an antibody-producing cell, and are therefore identical. Further, hybridomas that produce the inventive monoclonal antibodies against the immunogenic components of the MC4-R described herein can be produced by known techniques.

The following non-limiting Examples set forth the materials and methods utilized in the production of the inventive antibodies, and in the in vitro and in vivo experimentation conducted thereon.

EXAMPLE I

Materials and Methods

A. Production of mAbs against the MC4-R
1. NT4 and NT3 Peptide Synthesis

Figure 2:
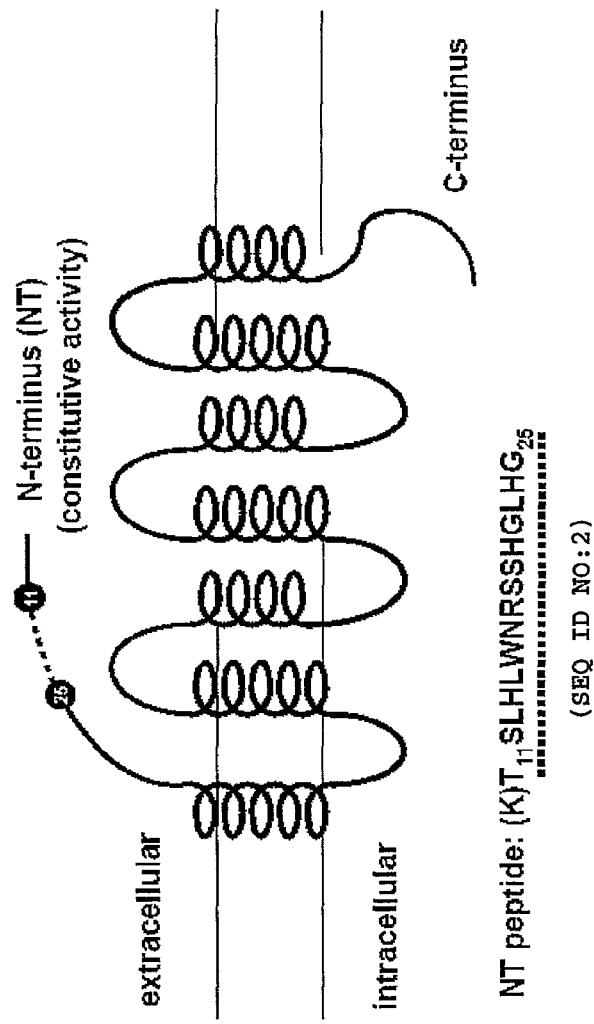
FIG. 2 illustrates the location and amino acid sequence (SEQ ID NO:2) of the N-terminal domain of the MC4-R.

The amino acid sequence of the rate MC4-R consists of 332 amino acid residues (SEQ ID NO:1; NCBI Accession No. NP037231) as shown in FIG. 1. In the present invention, peptides corresponding to the N-terminal domain of the MC4-R ("NT4 peptide", illustrated in FIG. 2) and N-terminal domain of the MC3-R ("NT3 peptide") were synthesized. The NT4 peptide has the amino acid sequence TSLHL-WNRSSHGLHG (SEQ ID NO:2) consisting of residues 11-25 of the rat MCR4-R (see Peter J C et al., Am. J. Physiol. Regul. Integr. Comp. Physiol. Biol. 2007; 292(6):R2151-8). The NT3 peptide has the amino acid sequence ASNRSGSG-FCEQVFIKPEV (SEQ ID NO:3) consisting of residues 26-44 of the rat MC3-R (SEQ ID NO:3). The peptides were synthesized as set forth in Neimark J and Briand J P, Pept. Res. 1993; 6(4):219-28.

2. Immunization

C58BL/6 mice were immunized with 25 μg of the free peptide NT4 emulsified in complete Freund's adjuvant and injected subcutaneously. Four weeks post-immunization, a booster injection of 25 gg in incomplete Freund's adjuvant was given. Four weeks later 10 gg peptide dissolved in NaCl 0.9% was injected intravenously three days before harvesting the spleen cells for fusion.

Hybridoma Formation

Fusion was performed with polyethylene glycol 1500 (Sigma, Saint-Louis, USA) at a ratio of 2 splenocytes for 1 myeloma cell. Hybridomas were cultivated in 96 well plates precoated with peritoneal macrophages of C58B16 mice 1000 cells/well. 5×105 cells were distributed per well in IMDM medium supplemented with 10% heat inactivated fetal calf serum, 200 mM glutamine, 1 00 mM sodium pyruvate, 1% penicillin streptomycin (Omnilab, Mettmenstetten, Switzerland) 3% Hypoxanthine, Aminopterine, Thymidine (HAT, Gibco, Lucerne, Switzerland) in a humidified incubator at 37° C. under an atmosphere of 5% $CO_2$.

Secreting clones were screened by enzyme immunoassay and subcloned by limiting dilution according to Oi V T, et al., J. Exp. Med. 1980; 151(5):1260-74.

4. Enzyme Immunoassay

NT4 peptide (2 μM) was adsorbed with carbonate buffer ($Na_2CO_3$ 15 mM, $NaHCO_3$ 35 mM, pH 9.6), an 96-well MAXISORP microtiter plates (Nunc, Roskilde, Denmark), 50 gl/well, by incubating for 2 h at 37° C. Plates were saturated with Phosphate Buffered Saline (PBS) ($Na_2HPO_4$ 10 mM, NaCl 150 mM, KCl 27 mM, pH 7.4) supplemented with 3% dried milk (Biorad, Hercules, Calif., USA) and 0.05% Tween 20 (Fluka, Buchs, Switzerland) (PBS-T milk) for 1 hat 37° C.

Immunized mice sera or 1:10 dilution of hybridoma culture supernatant were added to the plates and incubated for ih at 37° C. Plates were then washed with PBS containing 0.05% Tween 20 (PBS-T) and incubated with goat anti-mouse immunoglobulin H+L horseradish peroxidase conjugated (Biorad), diluted 1/5000, for 1 h at 37° C. After washing the plates with PBS-T and PBS, enzymatic reactions were carried out at room temperature by adding 3,3',5,5'tetramethylbenzidine (TMB) in the presence of 0.04% $H_2O_2$. Reactions were stopped after 15 min by the addition of HCl (1N). Optical density was measured at 450 nm by using a microplate reader Victor Wallac (Perkin Eimer, Fremont, Calif., USA).

B. mAb Characterization
1. cDNA Cloning of mAb Variable Domains

Total RNA was prepared from 107 freshly subcloned hybridoma cells using the RNAnow kit (Biogentex, USA) and first strand cDNA was synthesized using iScript™ cDNA Synthesis kit (Biorad, Hercules, Calif., USA). The VH and VL chain domains were amplified by PCR using IgG primer set (Novagen). The 50 gl PCR mixtures contained 50 ng hybridoma cDNA, 20 pmol of each appropriate primer, 250 µM of each dNTP, 1 xTaq buffer (Sigma) and 1 U *Thermus aquaticus* (Taq) polymerase.

Amplification included 50 cycles of 1.5 min at 94° C., 2.5 min at 55° C. and 3 min at 72° C. in a thermocycler (PTC-150, MJ Research). The amplified DNAs were ligated into the pGEMT vector (Promega, Madison, Wis., USA) and the recombinant plasmids purified using miniprep kit (Qiagen). The DNA sequences of the cloned VH and VL inserts were determined using the PRISM Cycle Sequencing kit (ABI) and M13 Forward and Reverse primers. The sequences of the V genes were determined on two independent batches of RNA preparations to ensure accuracy.

2. Isotyping

The isotype of the selected mAbs was determined using MonoAbiD kit according to manufacturer's instructions (Zymed lab).

3. mAb Purification

The anti-NT4 mAbs were affinity-purified on NT4 peptide coupled by their N-terminus end to activated CNBr-Sepharose 4B column (Amersham Biosciences, Uppsala, Sweden) according to manufacturer's instructions. Culture supernatants were loaded on the column at 4° C. The mAbs were eluted with 0.2 M glycine pH 2.7, collected in tubes containing 1 M Tris buffer pH 8, subsequently dialyzed against PBS overnight at 4° C. and finally stored at −20° C.

C. Assays

1. Cell Cultures

HEK-293 cells expressing human (h) MC4-R were cultured in Dulbecco's Modified Eagle Medium (DMEM) (Sigma, St. Louis, Mo., USA) containing 10% fetal calf serum (Bioconcept, Allschwil, Switzerland), 1% penicillin/streptomycin (Gibco, Grand Island, N.Y., USA) and G418 at 600 µg/ml (Sigma) in a humidified atmosphere containing 5% $CO_2$ at 37° C.

2. cAMP Assays

Cells were transferred to 24-well culture plates 12 h before treatment, then washed for 3 h with culture medium (DMEM, Sigma) and incubated for 30 min in PBS supplemented with 0.1% BSA and 3-isobutyl-1-methylxanthine (IBMX) (Sigma). Cells were treated with serial dilutions of purified mAbs for 30 min or preincubated with 100 nM of mAbs for 30 min and then treated with serial dilutions of a-melanocyte stimulating hormone (a-MSH, 10-9 to 10-5M) for 15 min.

Subsequently, cells were lysed with Biotrak cAMP lysis buffer and CAMP was measured using the Biotrak cAMP enzyme immunoassay System (Amersham Bioscience, Uppsala, Sweden) according to the manufacturer's instructions. Protein concentration was determined using the BCA kit (Pierce, Rockford, Ill., USA). The concentration of cAMP was expressed in fmol cAMP/µg protein.

3. Intracerebroventricular Cannulation

Male Sprague-Dawley rats (275 g to 325 g) were anaesthetized with isoflurane in medicinal oxygen (4% for induction and 2% for maintenance of anaesthesia). A stainless steel cannula (26 gauge, 10 mm long) was implanted into the third cerebral ventricle using the following coordinates, relative to the Bregma: −2.3 mm anteroposterior, 0 mm lateral to the midline, and −7.5 mm ventral to the surface of the skull.

The guide cannula was secured in place with 3 stainless steel screws and glass-ionomer cement (3M), and a stylet was inserted to seal the cannula until use. Temgesic (0.03 mg/kg) was given subcutaneously for 2 days post-surgery. Seven days after recovery from surgery, accuracy of the cannula placement in the third ventricle was tested by measuring the dipsogenic response (immediate drinking of at least 5 ml water in 15 min) to an icv injection of 20 pmol of angiotensin II in 5 pl injection volume.

4. Intracerebroventricular Injections

Purified mAbs were slowly (1 min) injected icv at 9:00 am at a dose of 0.1 µg in a volume of 5 pl using a Hamilton syringe. These doses were selected based on the results of comparative in vitro studies. Following the injection of rat Abs, food intake was continuously recorded during the following 3 days using an automatic food intake apparatus (TSE Systems, Bad Homburg, Germany) at one hour intervals for 3 days. After the injection of rabbit Abs, food intake was measured during the following 3 days at 9:00 am and 5:00 pm.

D. Data Analysis

All data are expressed as mean±SD or SEM as indicated. Data were analysed by two way ANOVA repeated measures with Bonferroni post-hoc test or by Student t-test using Graph pad Prism 4 software. For the cAMP concentration-response experiments, the best fitting curves were compared for their minimum, maximum and EC50 using F-test.

EXAMPLE II

Results

A. Peptide Specificity of the mAbs

Figure 3A:
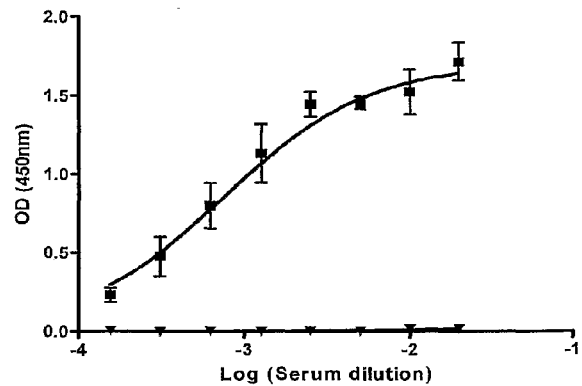
FIG. 3A shows the specificity of mouse serum used in hybridoma production for immunogenic peptide NT4 and peptide NT3.
Figure 3B:
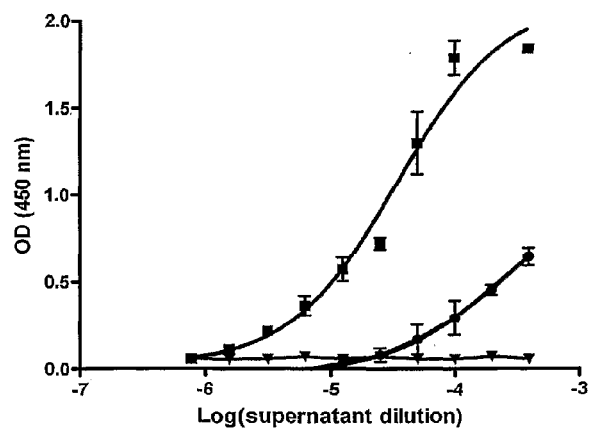
FIG. 3B shows the specificity of monoclonal antibody 1E8a for the immunogenic peptide NT4.

The enzyme immunoassay was performed an the free peptides NT4 and NT3. As shown in FIG. 3A, the serum of the mouse used for hybridoma production showed a highly specific and pronounced response against the immunogenic peptide NT4 derived from the N-terminus part of the MC4-R but not against the NT3 peptide derived from the N-terminus part of the MC3-R. Although the polyclonal response was high, only two clones could be conserved until subcloning and amplification: mAb 1E8a and mAb 2G2 both IgM antibodies. As shown in FIG. 3B, the specificity of mAb 1E8a for the NT4 peptide corresponded to the polyclonal mouse response.

B. Sequence of the Paratopes

The variable domain of the heavy and light chains of mAb 1E8a, and the variable domain of the heavy chain of mAb 2G2, were cloned and sequenced.

The nucleic acid and encoded amino acid sequences of the variable domain of the heavy chain of mAb 1E8a are shown in FIG. 4A (SEQ ID NO:4) and FIG. 4B (SEQ ID NO:5), respectively, with the complementary determining region indicated by underlining. The nucleic acid and encoded amino acid sequences of the variable domain of the light chain of mAb 1E8a are shown in FIG. 5A (SEQ ID NO:6) and FIG. 5B (SEQ ID NO:7), respectively, with the complementary determining region indicated by underlining.

The nucleic acid and encoded amino acid sequences of the variable domain of the heavy chain of mAb 2G2 are shown in FIG. 6A (SEQ ID NO:8) and FIG. 6B (SEQ ID NO:9), respectively, with the complementary determining region indicated by underlining. The constant regions of mAbs 1E8a and 2G2 are common to all mouse antibodies in this subtype.

C. In Vitro Pharmacological Activity of mAb 1E8a and mAb 2G2

Figure 7A:
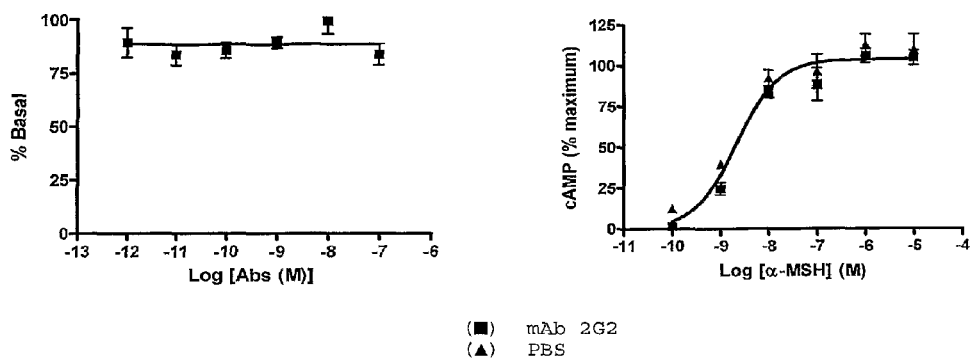
FIG. 7A shows the in vitro pharmacological activity of monoclonal antibody 2G2 in HEK-293 cells transfected with the MC4-R.

In order to detect inverse agonist activity of both mAbs, HEK-293 cells were treated with purified mAb 2G2 and mAb 1E8a. As shown in the concentration-response curves in FIG. 7A (left panel), when HEK-293 cells transfected with the MC4-R were exposed to increasing concentrations of mAb 2G2 (1 pM-0.1 µM), no decrease in cAMP was measured. As shown in FIG. 7A (right panel), the presence of mAb 2G2 had no effect on the concentration-response curve of a-MSH.

Figure 7B:
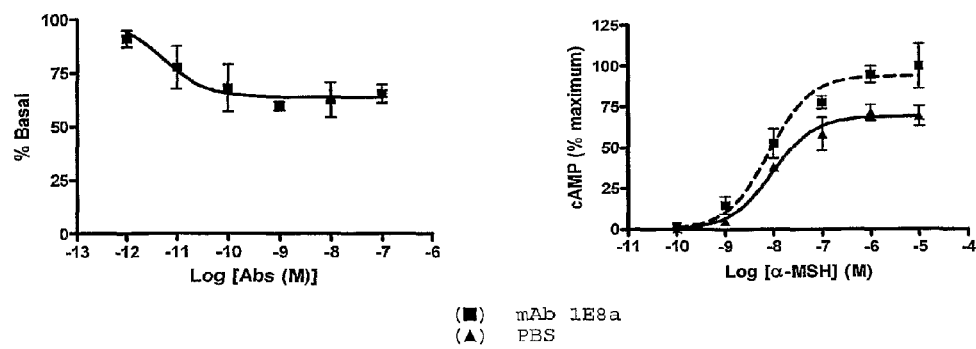
FIG. 7B shows the in vitro pharmacological activity of monoclonal antibody 1E8a in HEK-293 cells transfected with the MC4-R.

Conversely, as shown in FIG. 7B (left panel), when HEK-293 cells transfected with the MC4-R were exposed to increasing concentrations of mAb 1E8a (1 pM-0.1 MM) cAMP formation decreased in a concentration-dependent manner by up to 40%, and while the presence of mAb 2G2 did not change the concentration response curve of a-MSH, the presence of 100 nM of mAb 1E8a significantly ($p<0.001$, F-test) reduced the maximum effect of a-MSH, as shown in FIG. 7B (right panel). The concentration-dependent decrease in the intracellular cAMP content shows an inverse agonist effect of the mAb 1E8a.

The reduced maximum efficacy in the presence of mAb 1E8a suggests that it acts as a non-competitive antagonist. Data are presented as means±SD as calculated from 3 independent experiments.

Figure 8A:
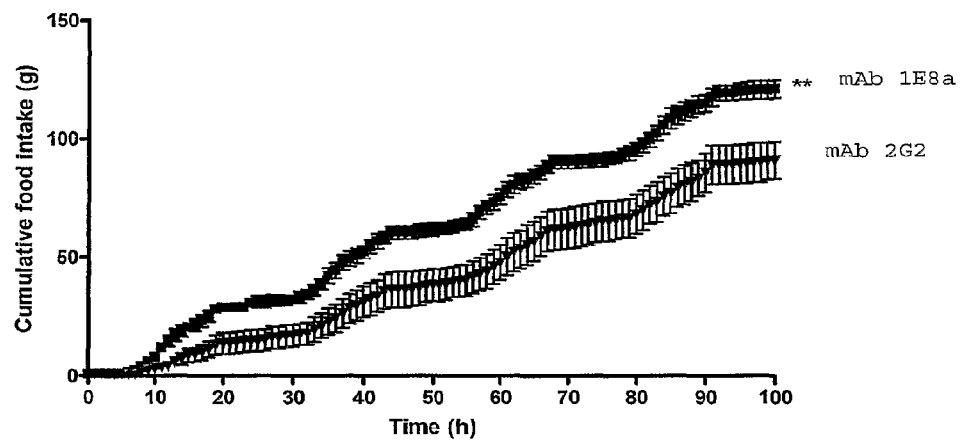
FIGS. 8A and 8B show the in vivo pharmacological activity of monoclonal antibodies 1E8a and 2G2 in rats.
Figure 8B:
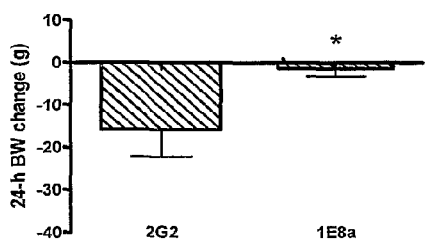

In Vivo Pharmacological Activity of mAb 1E8a and mAb 2G2 0.1 gg of purified mAb 2G2 and 1E8a Abs were injected into the third ventricle of rats. As shown in FIG. 8A, rats which received 1 µg of mAb 1E8a ingested 33% more food in 96 h than rats which received mAb 2G2 inactive on the MC4-R (data are presented as means±S.E.M. **: $p<0.01$ repeated measures two-way ANOVA with Bonferroni post-hoc test, n=5).

As shown in FIG. 8E, the body weight of the rats which received mAb 1E8a were unchanged whereas body weight was reduced in rats which received mAb 2G2 (*: $p<0.05$, Students' t-test, n=5).

The specificity of mAb 1E8a has been demonstrated. In cultured HEK-293 cells expressing human MCR4 which have been stained with fluorescently labeled mAb 1E8a significant levels of expressed hMCR4 were detected. In in vitro cell cultures either HEK-293 cells expressing hMRC3 were stained in the same procedure as in or cells that expressed hMCR4 were stained with mAb 2G2 (control antibody). In both cases no significant staining occurred.

FIG. 9 summarizes the immuno-cytochemical staining of cells which express either MCR4 or MCR3 and which were stained with mAb 1E8A or mAb 2G2 (control mAb). In addition, the binding constant Kd of mAb 1E8a to the NT4 peptide was determined as $2.3 \times 10^{-9}$ M.

Figure 10:
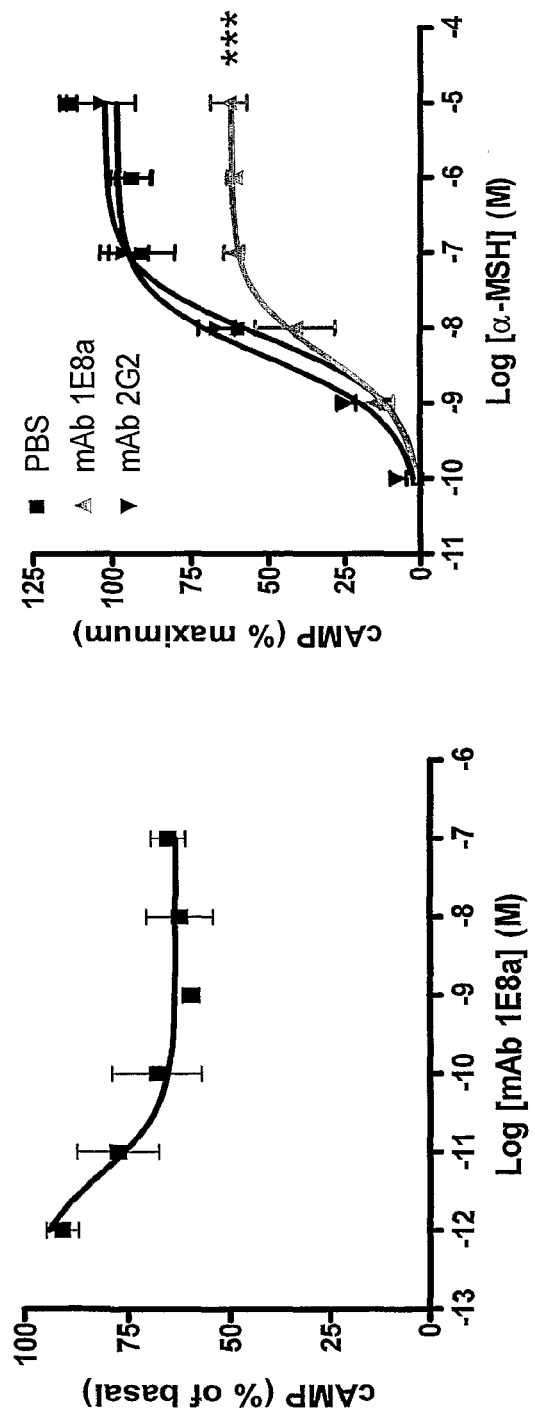
FIG. 10 shows the in vitro pharmacological activity of mAb 1E8a and 2G2.

FIG. 10 shows the in vitro pharmacological effects of mAb 1E8a and the control mAb 2G2 on cAMP. While the addition of increasing amounts of mAb 1E8a clearly led to a decrease in intracellular cAMP levels (left panel) and also diminished the concentration-response curve of α-MSH, mAb 2G2 and PBS (phosphate buffered saline), which were both used as controls, had no significant effect on the concentration response curve of α-MSH (right panel). The results are comparable to those shown in FIGS. 7A and 7B. Data are presented as mean±SD, n=3; ***:$p<0.001$, Two-way ANOVA repeated measures.

Figure 11:
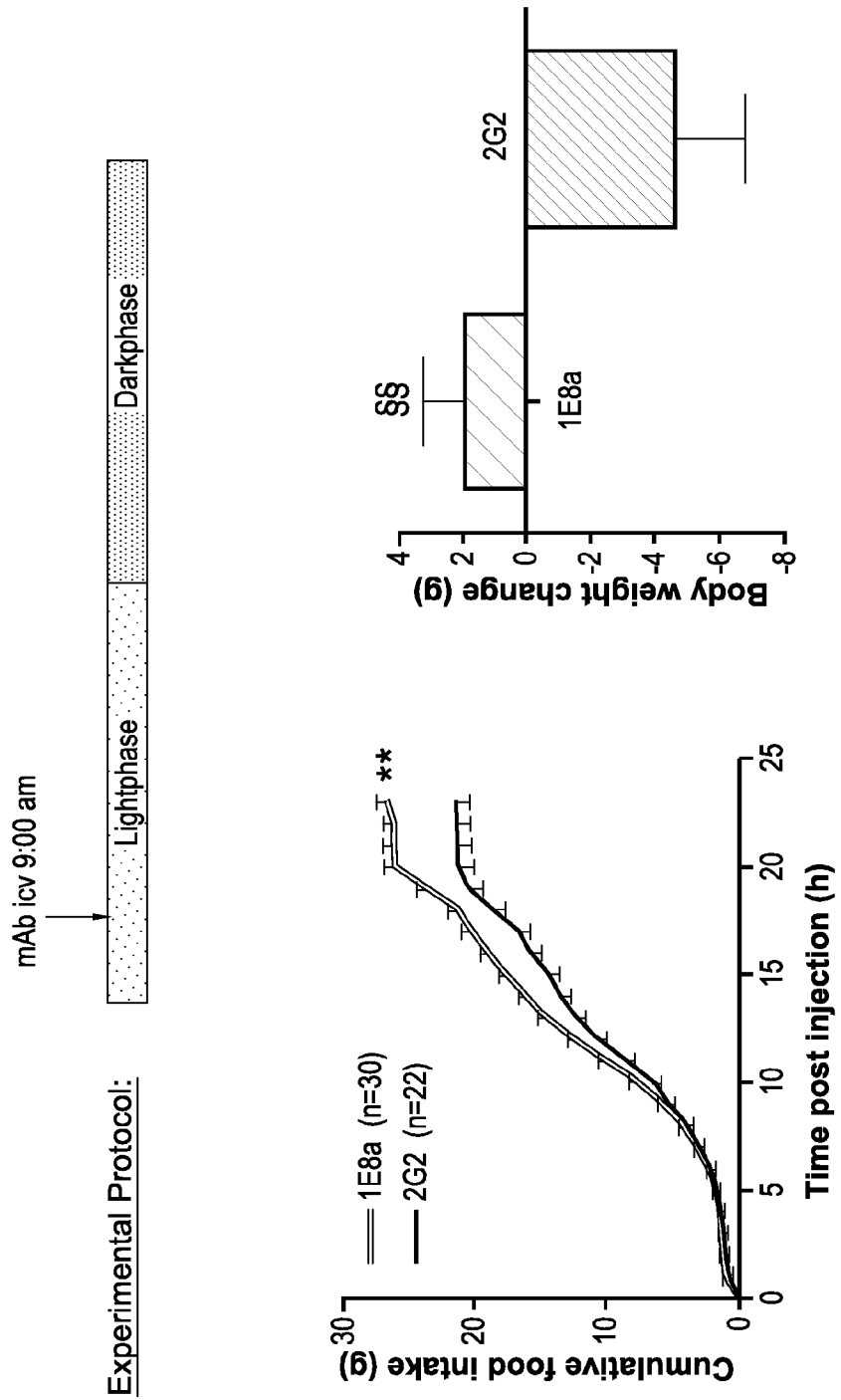
FIG. 11 shows the in vivo effect of mAb 1E8a and 2G2 (1 μg) after intracerebroventricular (icv) injection of the mAbs.

FIG. 11 shows the in vivo effect of mAb 1E8a and 2G2 (1 µg) after intracerebroventricular (icv) injection of the mAbs. The monoclonal antibodies were both administered at 9:00 am during the light phase (experimental protocol) as indicated above. The results are presented as mean±S.E.M, **: $p<0.01$; Two-way ANOVA repeated measures, Bonferroni post-hoc test; §§: $p<0.01$, Student t-test. The left panel of FIG. 11 shows that administration of mAb 1E8a leads to a significant increase in food uptake measured during the post injection phase compared to the mAb 2G2. The right panel illustrates the body weight change. Rats which were injected with mAb 1E8a did not suffer from body weight loss during the post injection phase. On the contrary, their body weight increased. On the other hand, Rats that were injected with mAb 2G2 showed a significant loss in body weight during the post injection phase.

Figure 12:
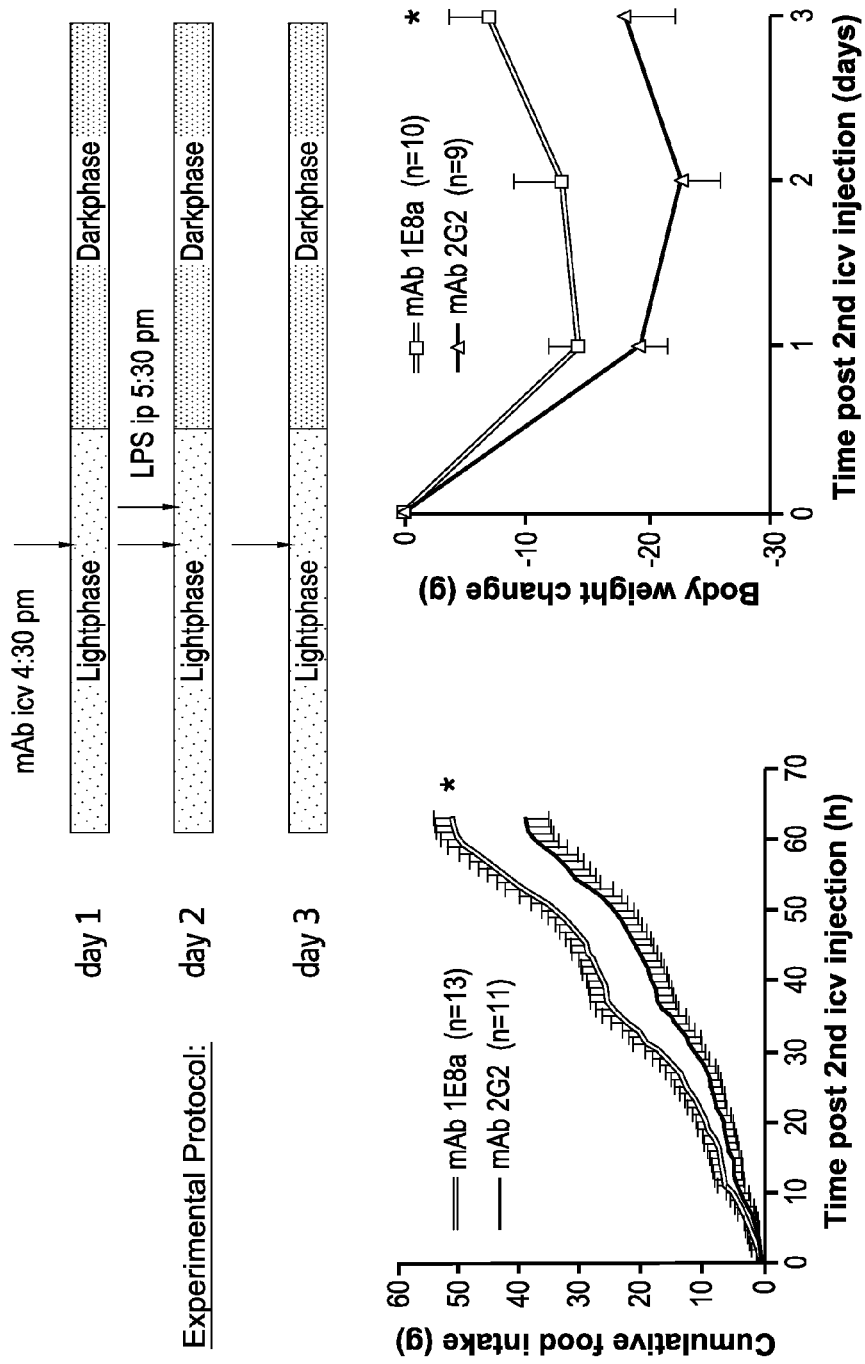
FIG. 12 shows the in vivo effect of intracerebroventricular injection of mAb 1E8a and 2G2 (1 μg)+intraperitoneal (ip) injection of LPS.

In FIG. 12 the in vivo effect of intracerebroventricular (icv) injection of mAb 1E8a and 2G2 (1 µg)+intraperitoneal (ip) injection of LPS is shown. Again, the results are presented as mean±S.E.M, * :$p<0.05$, Two-way ANOVA repeated measures, Bonferroni post-hoc test. The experimental protocol comprised the intracerebroventricular injection of either mAb 1E8a or 2G2 at 4:30 pm during the light phase on three consecutive days. On the second day LPS (lipopolysaccharide) was injected intraperitoneally (ip). The rats that were administered the (active) mAb 1E8a did not only show an increased food uptake measured after the second icv injection, in addition their body weight loss was significantly reduced compared to the control group of rats which were injected with the mAb 2G2.

Figure 13:
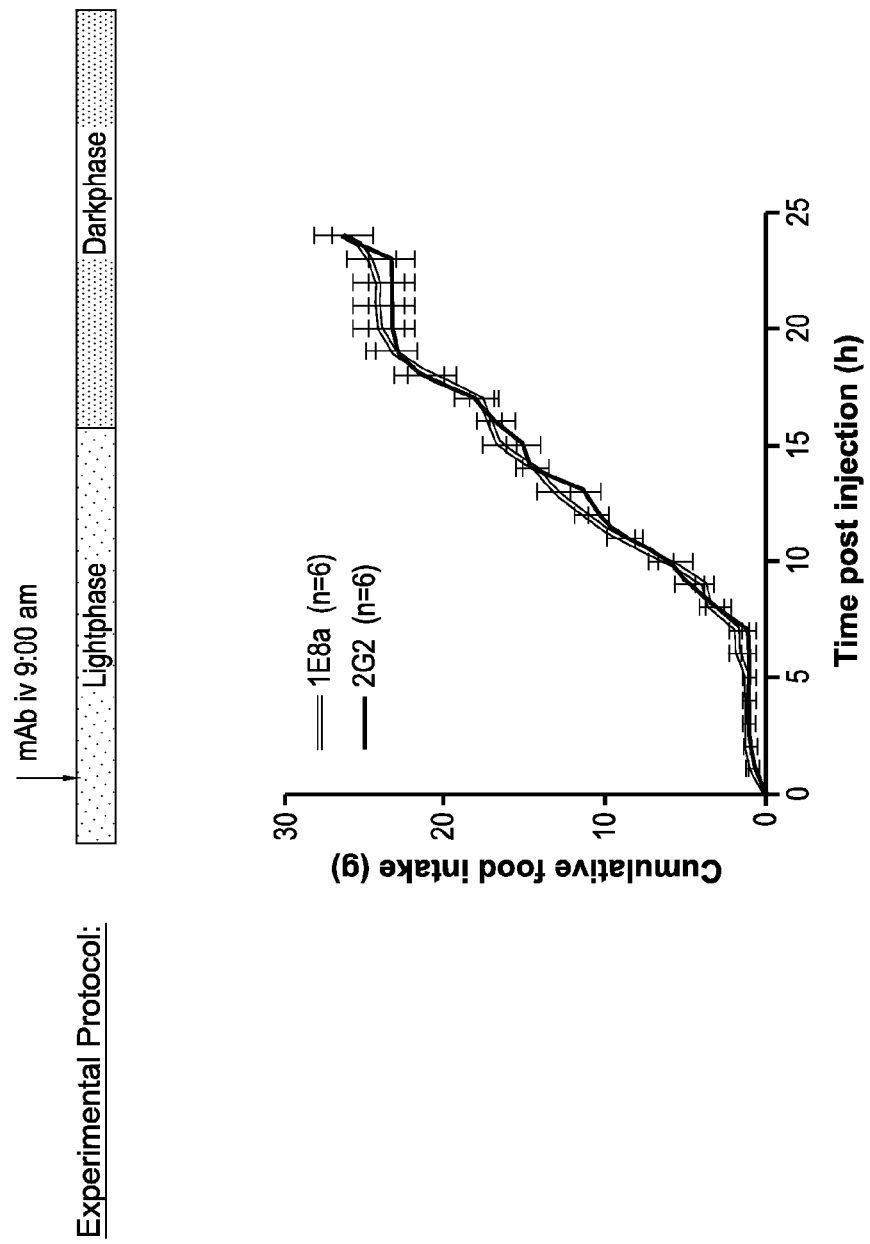
FIG. 13 shows the in vivo effect of intravenous (iv) injection of mAb 1E8a and 2G2 (300 μg/kg).

FIG. 13 shows the in vivo effect of intravenous (iv) injection of mAb 1E8a and 2G2 (300 µg/kg). The results are presented as mean±S.E.M. The experimental protocol comprised an intravenous (iv) injection with either mAb (1E8a or 2G2). The injection was performed at 9:00 am in the light phase. No significant difference in the cumulative food intake could be detected between the two groups.

Figure 14:
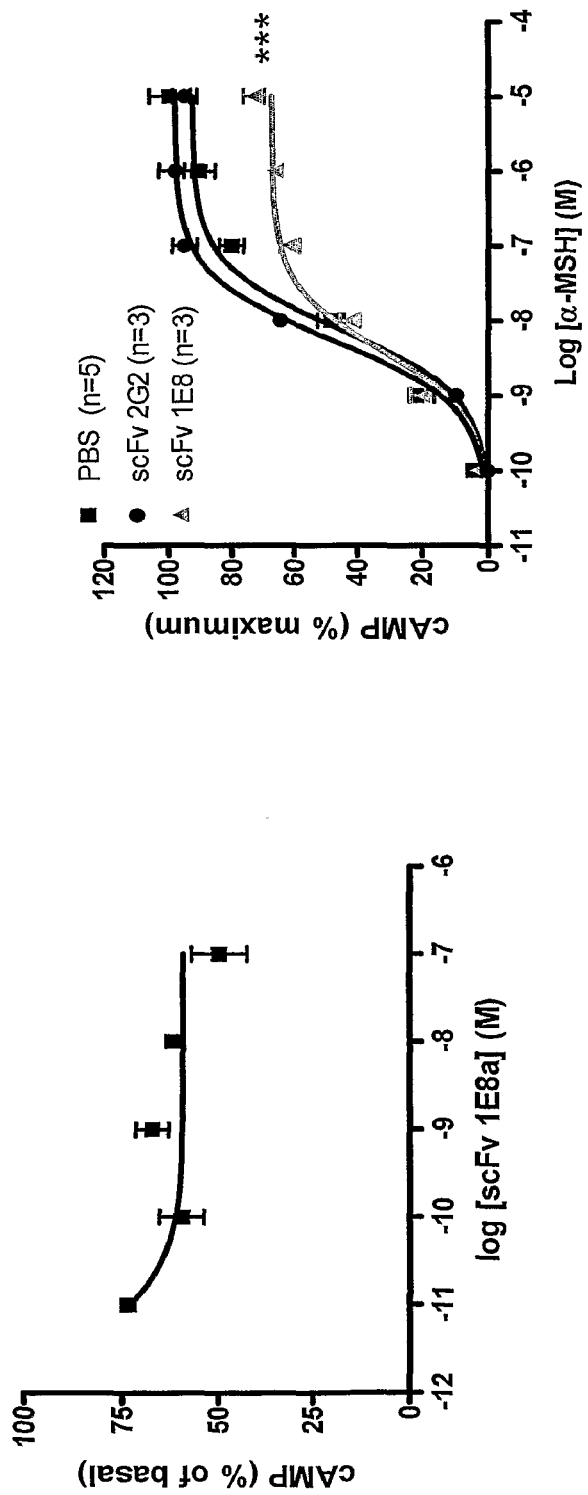
FIG. 14 shows the in vitro Effects of scFv 1E8a and 2G2.

FIG. 14 shows the in vitro Effects of single chain Fv fragments (scFv) of 1E8a and 2G2 on cAMP levels. PBS was used as a further control and, as well as scFv of 2G2, it did not influence the concentration response curve of α-MSH. The results are similar to those shown in FIG. 10.

Figure 15:
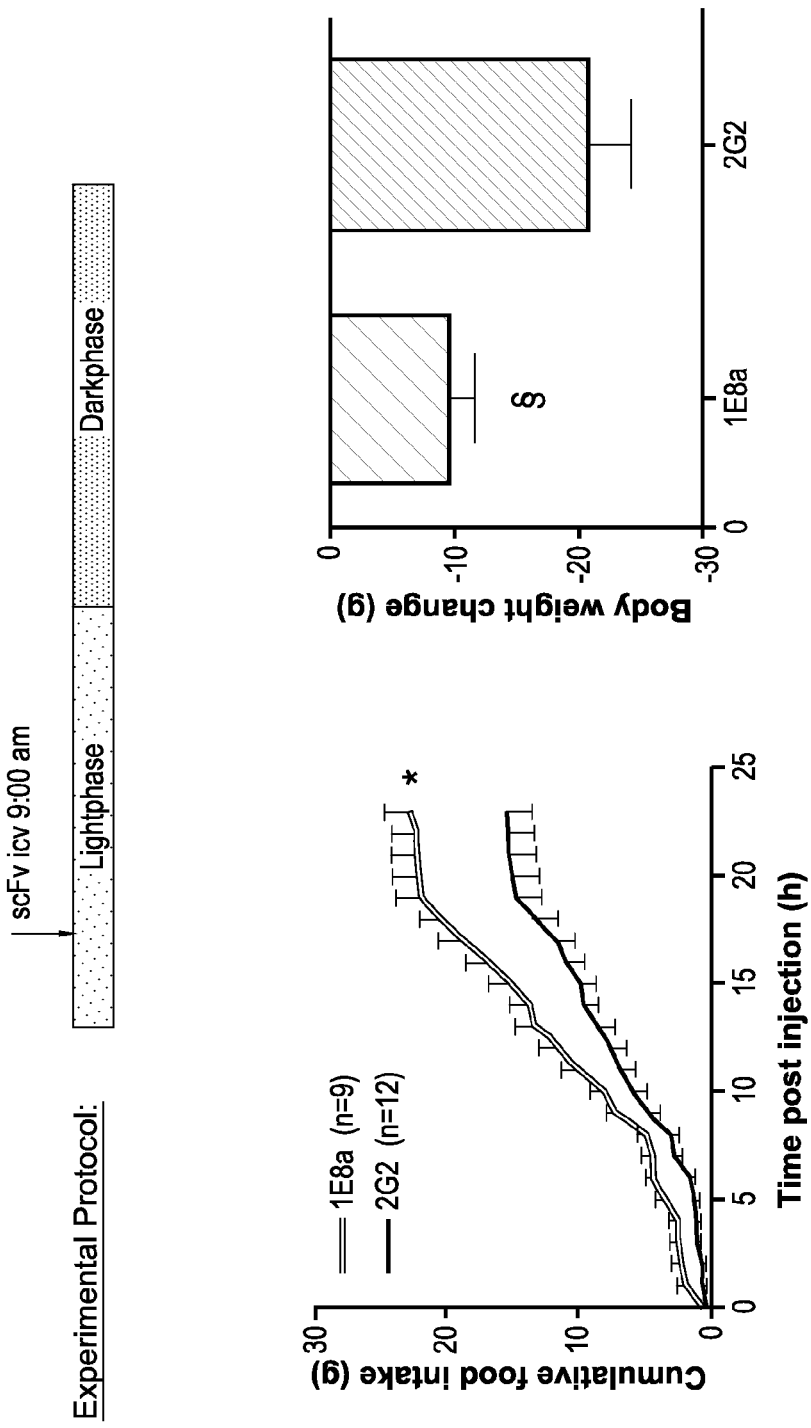
FIG. 15 shows the in vivo effect of icv injection of single chain fragments (scFv) of mAb 1E8a and 2G2 (1.7 μg).

FIG. 15 shows the in vivo effect of icv injection of single chain fragments (scFv) of mAb 1E8a and 2G2 (1.7 µg). The results are presented as mean±S.E.M, *: $p<0.05$, Two-way ANOVA repeated measures, Bonferroni post-hoc test, §: $p<0.05$, Student t-test.

According to the experimental protocol the scFv were injected intracerebroventricularly at 9:00 am during the light phase. The administration of scFv of 1E8a did significantly increase the cumulative food uptake which was measured in the post injection period. However, both groups of rats showed loss in body weight during the post injection period. However, the body weight loss in rats which were administered the scFv of 1E8a showed a significantly reduced body weight loss.

Figure 16:
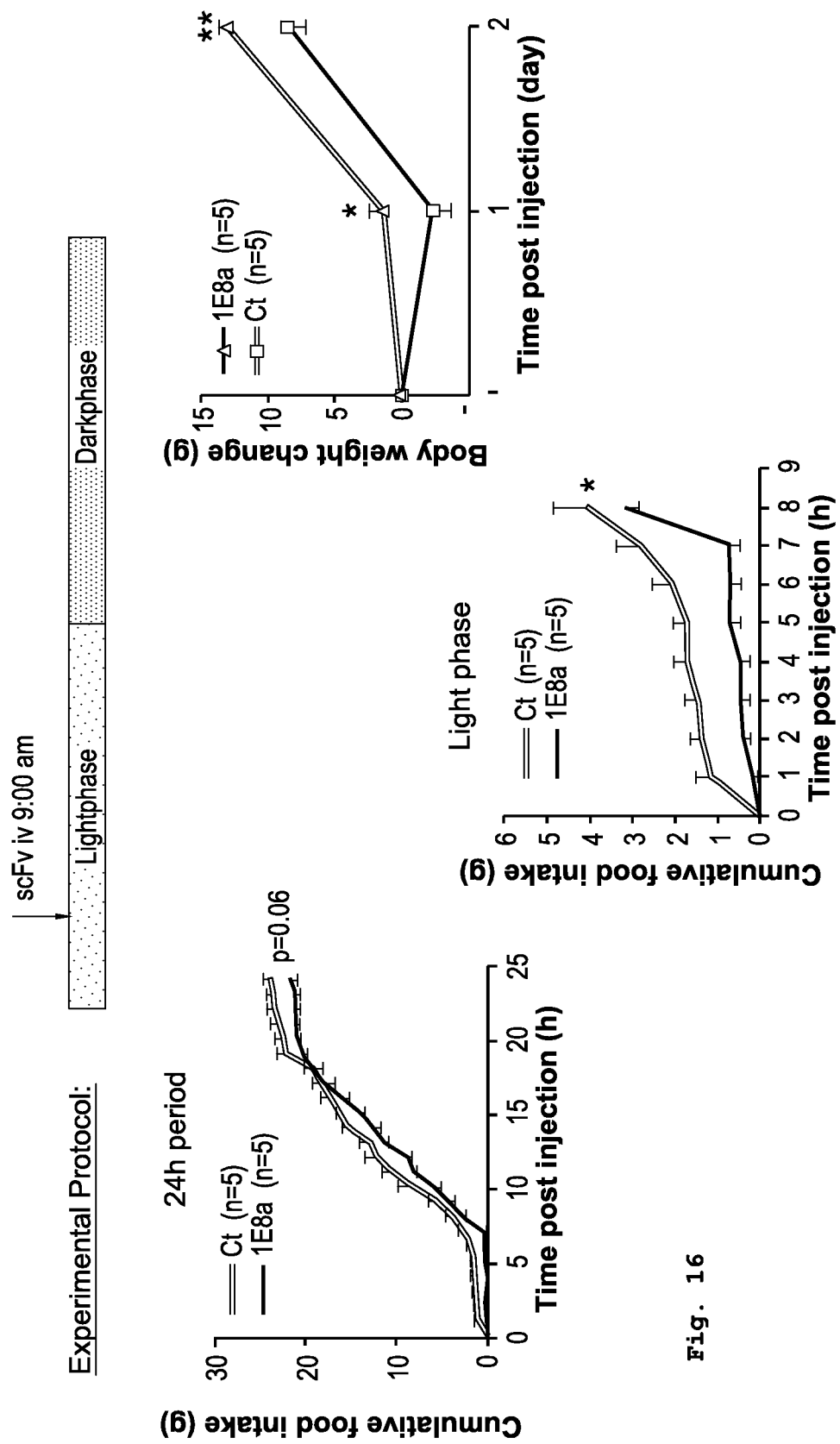
FIG. 16 shows the in vivo effect of iv injection of scFv 1E8a (300 μg/kg).

In FIG. 16 the in vivo effect of iv injection of scFv 1E8a (300 µg/kg) is shown. The results are presented as mean±S.E.M; *:$p<0.05$, **: $p<0.01$, Two-way ANOVA repeated measures, Bonferroni post-hoc test; Ct means inactive eluate, 1E8a designates the active eluate. According to the experimental protocol of scFv of 1E8a or 2G2 are injected intravenously (iv) at 9:00 am during the light phase. The scFv of 1E8a caused a significantly higher cumulative food intake during the light phase (middle panel) as well as a higher body weight change during post injection phase.

Figure 17:
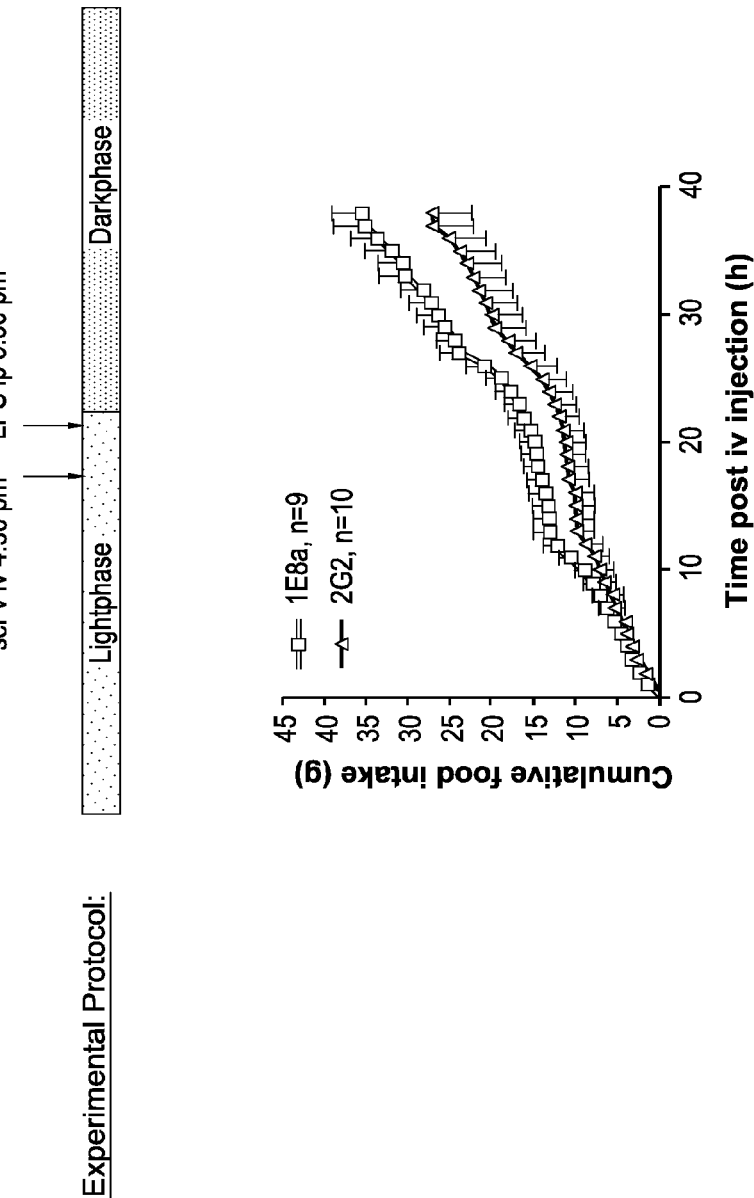
FIG. 17 shows the in vivo effect of iv Injection of scFv 1E8a and 2G2+intraperitoneal (ip) Injection of LPS (300 μg/kg).

FIG. 17 shows the in vivo effect of iv Injection of scFv 1E8a and 2G2+ip Injection of LPS (300 µg/kg). The results are presented as mean±S.E.M. The experimental protocol comprises a intravenous (iv) injection of scFv of either 1E8a or 2G2 at 4:30 pm and, one hour later, at 5:30 pm an intraperitoneal (ip) injection of LPS. Rats that were treated with scFv of 1E8a show a clear tendency of an increased cumulative food intake observed in the time period post injection of scFv.

FIG. 18 shows the amino acid sequence of cyclic peptides H1 (SEQ ID NO: 10), H2 (SEQ ID NO: 11), H3 (SEQ ID NO: 12), L1 (SEQ ID NO: 13), L2 (SEQ ID NO: 14) and L3 (SEQ ID NO: 15).

Figure 19:
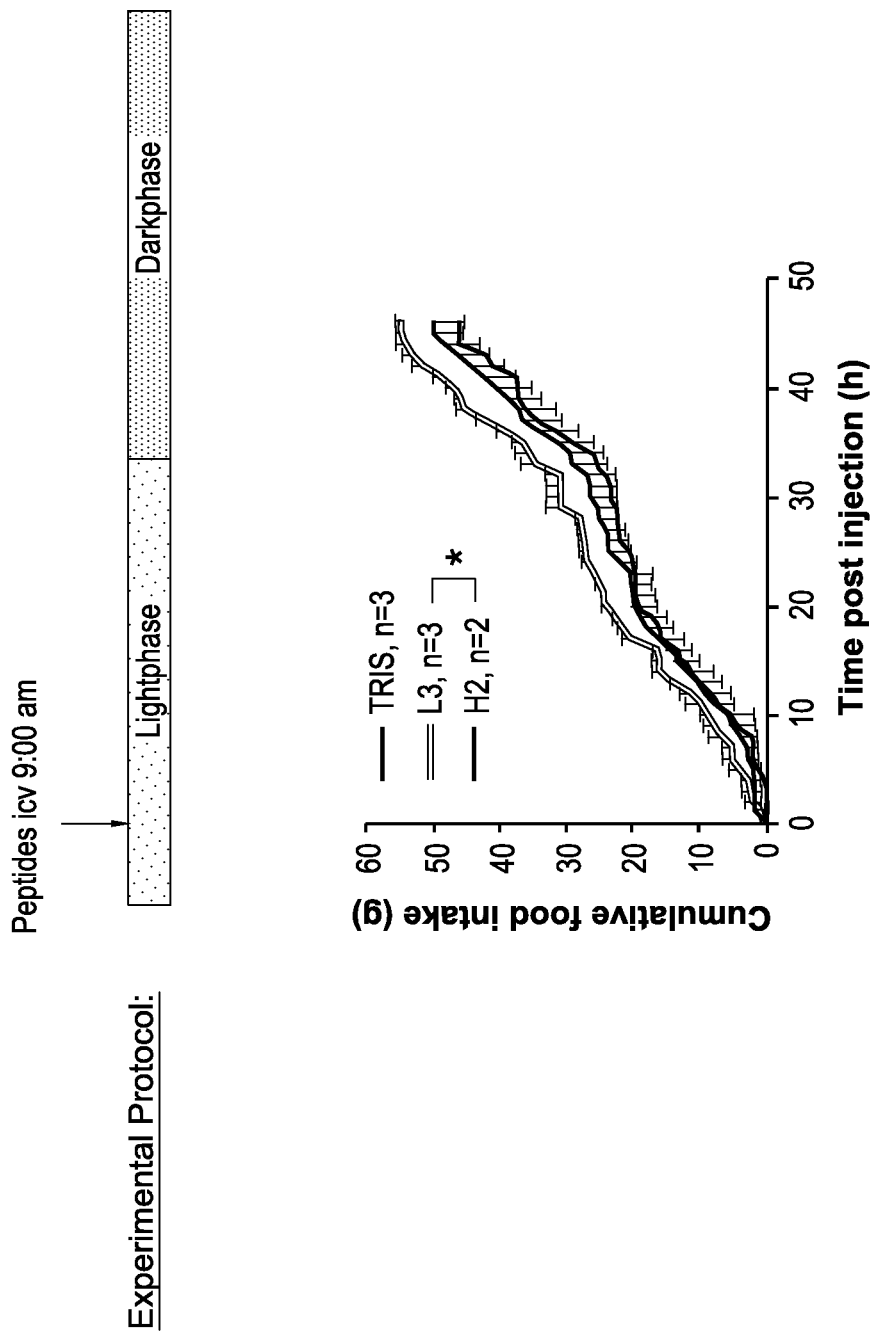
FIG. 19 shows the in vivo effect of icv injection of cyclic peptides L3 and H2 (1 μg).

In FIG. 19 the in vivo effect of intracerebroventricular (icv) injection of cyclic peptides L3 and H2 (1 µg) is shown. The results are presented as mean±S.E.M,*:$p<0.05$, Two-way ANOVA repeated measures, Bonferroni post-hoc test.

According to the experimental protocol the peptides L3 and H2 were administered at 9:00 a.m. during the light phase. TRIS buffer was used as a further control. The cyclic peptide L3 shows a tendency to increase the cumulative food intake observed in the post injection phase.

FIG. 20 shows the amino acid sequences of the mAb Paratope of mAb 1E8a. The upper panel shows the amino acid sequence of the variable domain of the heavy chain (SEQ ID NO: 16) and the lower panel shows the amino acid sequence of the variable domain of the light chain (SEQ ID NO 17).

As shown in the Examples above, mAbs produced against the MC4-R, in particular mAb 1E8a, have a profound effect an appetite and, resultantly, weight loss, indicating their therapeutic utility for cachexia and related conditions and diseases.

The inventive therapeutic mAbs may be administered in any known, suitable way. For example, in certain embodiments they may administered according to standard monoclonal antibody therapy protocols where they are infused in a clinical setting to specifically target cells expressing the MC4-R. In some embodiments they may be administered parenterally, orally or administered to the sinuses, throat or lungs, and respectively in a suitable form for such administration. They may further be modified in certain embodiments according to art recognized techniques, for example they may be chimerized and humanized for various therapeutic purposes.

Further, they may be provided in combination with other active therapeutic agents, and in certain embodiments may form immunoconjugates to direct other therapeutic agents to the MC4R. Once given the teachings provided herein, those of skill in the art will be able to determine such methods and forms of administration, combinations, and so forth.

Likewise, one skilled in the art will be able to determine the proper dosing of such therapeutic agents and formulations using art-recognized techniques (factors known to effect dosing regimens include, for example and without limitation, the pharmacodynamic characteristics of the particular agent and its mode and route of administration; the species, age, sex, general health, medical condition, diet, and body weight of the recipient; the nature and extent of the Symptoms; the kind of concurrent treatment; the frequency of treatment; the time of administration; route of administration, the renal and hepatic function of the patient, and the effect desired). Further, fragments and derivatives (including homologues, analogues, etc.) of the mAbs disclosed herein having the desired therapeutic activity against MC4-R are within the scope of the present invention and can be used in the formulation of therapeutic compounds.

As various changes can be made in the above compositions and methods without departing from the scope and Spirit of the invention, it is intended that all subject matter contained in the above description, shown in the accompanying drawings, or defined in the appended claims be interpreted as illustrative, and not in a limiting sense.

The contents of all patents, patent applications, published articles, books, reference manuals, texts and abstracts cited herein are hereby incorporated by reference in their entirety to more fully describe the state of the art to which the present invention pertains.

The invention claimed is:

1. A method for stimulating the appetite of a mammal having a reduced appetite, comprising administering to the mammal having reduced appetite, an isolated monoclonal antibody or binding fragment thereof that binds to the N-terminus of the melanocortin-4 receptor and wherein said isolated monoclonal antibody or binding fragment thereof comprises amino acid sequences set forth in SEQ ID NO:5 and/or SEQ ID NO:7, or
   amino acids 24 to 31 of SEQ ID NO:5, amino acids 49 to 56 of SEQ ID NO: 5, amino acids 94 to 107 of SEQ ID NO: 5, amino acids 24 to 34 of SEQ ID NO: 7, amino acids 50 to 57 of SEQ ID NO: 7 and amino acids 89 to 97 of SEQ ID NO: 7.

2. A method for treating symptoms of cachexia in a mammal, comprising administering to said mammal exhibiting said symptoms of cachexia a pharmaceutical composition comprising an isolated monoclonal antibody or binding fragment thereof that binds to the N-terminus of the melanocortin-4 receptor and wherein said isolated monoclonal antibody or binding fragment thereof comprises the amino acid sequences set forth in SEQ ID NO: 5 and/or SEQ ID NO:7, or
   amino acids 24 to 31 of SEQ ID NO:5, amino acids 49 to 56 of SEQ ID NO: 5, amino acids 94 to 107 of SEQ ID NO: 5, amino acids 24 to 34 of SEQ ID NO: 7, amino acids 50 to 57 of SEQ ID NO: 7 and amino acids 89 to 97 of SEQ ID NO: 7.

3. The method of claim 2, wherein said isolated monoclonal antibody or binding fragment thereof comprises the amino acid sequences set forth in SEQ ID NO:5 and SEQ ID NO:7.

4. A method for stimulating appetite according to claim 1, wherein said isolated monoclonal antibody or binding fragment thereof comprises the amino acid sequences set forth in SEQ ID NO: 5 and SEQ ID NO:7.

5. The method of claim 1, wherein said antibody or binding fragment thereof binds to a portion of the melanocortin-4 receptor comprising the amino acid sequence set forth in SEQ ID NO:2.

6. The method of claim 2, wherein said antibody or binding fragment thereof binds to a portion of the melanocortin-4 receptor comprising the amino acid sequence set forth in SEQ ID NO:2.

7. The method of claim 5, wherein the isolated monoclonal antibody or binding fragment comprises amino acids 24 to 31 of SEQ ID NO:5, amino acids 49 to 56 of SEQ ID NO: 5, amino acids 94 to 107 of SEQ ID NO: 5, amino acids 24 to 34 of SEQ ID NO: 7, amino acids 50 to 57 of SEQ ID NO: 7 and amino acids 89 to 97 of SEQ ID NO: 7.

8. The method of claim 6, wherein the isolated monoclonal antibody or binding fragment comprises amino acids 24 to 31 of SEQ ID NO:5, amino acids 49 to 56 of SEQ ID NO: 5, amino acids 94 to 107 of SEQ ID NO: 5, amino acids 24 to 34 of SEQ ID NO: 7, amino acids 50 to 57 of SEQ ID NO: 7 and amino acids 89 to 97 of SEQ ID NO: 7.

9. The method of claim 1, wherein the isolated monoclonal antibody or binding fragment thereof comprises the variable domain of a heavy chain of said isolated monoclonal antibody and the variable domain of a light chain of said isolated monoclonal antibody.

10. The method of claim 2, wherein the isolated monoclonal antibody or binding fragment thereof comprises the variable domain of a heavy chain of said isolated monoclonal antibody and the variable domain of a light chain of said isolated monoclonal antibody.

11. The method of claim 1, wherein said antibody or binding fragment thereof binds to a portion of the melanocortin-4 receptor comprising the amino acid sequence set forth in SEQ ID NO:2 comprising the amino acid sequences which are encoded by the nucleic acid sequences set forth in SEQ ID NO:4 and SEQ ID NO:6.

12. The method of claim 2, wherein said antibody or binding fragment thereof binds to a portion of the melanocortin-4 receptor comprising the amino acid sequence set forth in SEQ ID NO:2 comprising the amino acid sequences which are encoded by the nucleic acid sequences set forth in SEQ ID NO:4 and SEQ ID NO:6.

13. The method of claim 1, wherein the isolated monoclonal antibody or binding fragment thereof is an antagonist or a reverse agonist of the melanocortin-4 receptor.

14. The method of claim 2, wherein the isolated monoclonal antibody or binding fragment thereof is an antagonist or a reverse agonist of the melanocortin-4 receptor.

15. The method of claim 1, wherein said isolated monoclonal antibody or binding fragment thereof is produced recombinantly.

16. The method of claim 2, wherein said isolated monoclonal antibody or binding fragment thereof is produced recombinantly.

* * * * *

SEQUENCE LISTING

```
<160> NUMBER OF SEQ ID NOS: 17

<210> SEQ ID NO 1
<211> LENGTH: 332
<212> TYPE: PRT
<213> ORGANISM: Rattus norvegicus

<400> SEQUENCE: 1

Met Asn Ser Thr His His His Gly Met Tyr Thr Ser Leu His Leu Trp
1               5                   10                  15

Asn Arg Ser Ser His Gly Leu His Gly Asn Ala Ser Glu Ser Leu Gly
            20                  25                  30

Lys Gly His Ser Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
    50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Val Ile Thr Leu Leu Asn Ser Thr Asp Thr
            100                 105                 110

Asp Ala Gln Ser Phe Thr Val Asn Ile Asp Asn Val Ile Asp Ser Val
        115                 120                 125

Ile Cys Ser Ser Leu Leu Ala Ser Ile Cys Ser Leu Leu Ser Ile Ala
    130                 135                 140

Val Asp Arg Tyr Phe Thr Ile Phe Tyr Ala Leu Gln Tyr His Asn Ile
145                 150                 155                 160
```

```
Met Thr Val Arg Arg Val Gly Ile Ile Ile Ser Cys Ile Trp Ala Ala
            165                 170                 175

Cys Thr Val Ser Gly Val Leu Phe Ile Ile Tyr Ser Asp Ser Ser Ala
        180                 185                 190

Val Ile Ile Cys Leu Ile Thr Met Phe Phe Thr Met Leu Val Leu Met
            195                 200                 205

Ala Ser Leu Tyr Val His Met Phe Leu Met Ala Arg Leu His Ile Lys
        210                 215                 220

Arg Ile Ala Val Leu Pro Gly Thr Gly Thr Ile Arg Gln Gly Ala Asn
225                 230                 235                 240

Met Lys Gly Ala Ile Thr Leu Thr Ile Leu Ile Gly Val Phe Val Val
            245                 250                 255

Cys Trp Ala Pro Phe Phe Leu His Leu Leu Phe Tyr Ile Ser Cys Pro
            260                 265                 270

Gln Asn Pro Tyr Cys Val Cys Phe Met Ser His Phe Asn Leu Tyr Leu
        275                 280                 285

Ile Leu Ile Met Cys Asn Ala Val Ile Asp Pro Leu Ile Tyr Ala Leu
        290                 295                 300

Arg Ser Gln Glu Leu Arg Lys Thr Phe Lys Glu Ile Ile Cys Phe Tyr
305                 310                 315                 320

Pro Leu Gly Gly Ile Cys Glu Leu Pro Gly Arg Tyr
            325                 330

<210> SEQ ID NO 2
<211> LENGTH: 16
<212> TYPE: PRT
<213> ORGANISM: Rattus norvegicus

<400> SEQUENCE: 2

Lys Thr Ser Leu His Leu Trp Asn Arg Ser His Gly Leu His Gly
1               5                   10                  15

<210> SEQ ID NO 3
<211> LENGTH: 1
<212> TYPE: PRT
<213> ORGANISM: Rattus norvegicus

<400> SEQUENCE: 3

Lys
1

<210> SEQ ID NO 4
<211> LENGTH: 354
<212> TYPE: DNA
<213> ORGANISM: Rattus norvegicus

<400> SEQUENCE: 4
gagttccagc tgcagcagtc tggacctgag ctggtggagc ctggcgcttc agtgaagata      60
tcctgcaagg cttctggtta ctcattcact gactacaaca tgaactgggt gaagcagagc     120
aatggaaaga gccttgagtg gattggagta attaatccta actatggtac tactagctac     180
aatcagaagt tcaagggcaa ggccacattg actgtagacc aatcttccag cacagcctac     240
atgcagctca acagcctgac atctgaggac tctgcagtct attactgtgc aagatttgat     300
ggttactacg ttactacttt tgactactgg ggccaaggca ccactctcac agtc           354

<210> SEQ ID NO 5
<211> LENGTH: 116
<212> TYPE: PRT
<213> ORGANISM: Rattus norvegicus
```

-continued

<400> SEQUENCE: 5

Glu Phe Gln Gln Ser Gly Pro Glu Leu Val Glu Pro Gly Ala Ser Val
1               5                   10                  15

Lys Ile Ser Cys Lys Ala Ser Gly Tyr Ser Phe Thr Asp Tyr Asn Met
            20                  25                  30

Asn Trp Val Lys Gln Ser Asn Gly Lys Ser Leu Glu Trp Ile Gly Val
        35                  40                  45

Ile Asn Pro Asn Tyr Gly Thr Thr Ser Tyr Asn Gln Lys Phe Lys Gly
    50                  55                  60

Lys Ala Thr Leu Thr Val Asp Gln Ser Ser Thr Ala Tyr Met Gln
65                  70                  75                  80

Leu Asn Ser Leu Thr Ser Glu Asp Ser Ala Val Tyr Tyr Cys Ala Arg
                85                  90                  95

Phe Asp Gly Tyr Tyr Gly Tyr Tyr Phe Asp Tyr Trp Gly Gln Gly Thr
            100                 105                 110

Thr Leu Thr Val
        115

<210> SEQ ID NO 6
<211> LENGTH: 321
<212> TYPE: DNA
<213> ORGANISM: Rattus norvegicus

<400> SEQUENCE: 6
gacattgtga tgacccagtc tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat tacactcagg agtcccatca     180
aggttcagtg gcagtgggtc tggaacagat tattctctca ccattagcaa cctggagcaa     240
gaagatattg ccacttactt ttgccaacag ggtaatacgc ttccgtacac gttcggaggg     300
gggaccaagc tggaaataaa a                                               321

<210> SEQ ID NO 7
<211> LENGTH: 107
<212> TYPE: PRT
<213> ORGANISM: Rattus norvegicus

<400> SEQUENCE: 7

Asp Ile Val Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105

<210> SEQ ID NO 8
<211> LENGTH: 339
<212> TYPE: DNA
<213> ORGANISM: Rattus norvegicus

```
<400> SEQUENCE: 8
cagatccagt tggtgcagtc tggacctgag ctgaagaagc ctggagagac agtcaagatc    60
tcctgcaagg cttctgggta taccttcaca actgctggaa tgcagtgggt gcaaaagatg   120
ccaggaaagg gttttaagtg gattggctgg ataaacaccc actctggaga gccaaaatat   180
gcagaagact tcaagggacg gtttgccttc tctttggaaa cctctgccag cactgcctat   240
ttacagataa gcaacctcaa aaatgaggac acggctacgt atttctgtgc gagggggtta   300
ttactacggc tctggggcca agggactctg gtcactgtc                          339

<210> SEQ ID NO 9
<211> LENGTH: 113
<212> TYPE: PRT
<213> ORGANISM: Rattus norvegicus

<400> SEQUENCE: 9
```

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Ala
            20                  25                  30

Gly Met Gln Trp Val Gln Lys Met Pro Gly Lys Gly Phe Lys Trp Ile
        35                  40                  45

Gly Trp Ile Asn Thr His Ser Gly Glu Pro Lys Tyr Ala Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Ser Asn Leu Lys Asn Glu Asp Thr Ala Thr Tyr Phe Cys
                85                  90                  95

Ala Arg Gly Leu Leu Leu Arg Leu Trp Gly Gln Gly Thr Leu Val Thr
            100                 105                 110

Val

```
<210> SEQ ID NO 10
<211> LENGTH: 15
<212> TYPE: PRT
<213> ORGANISM: Rattus norvegicus

<400> SEQUENCE: 10
```

Cys Lys Ala Ser Gly Tyr Ser Phe Thr Asp Tyr Asn Met Asn Cys
1               5                   10                  15

```
<210> SEQ ID NO 11
<211> LENGTH: 19
<212> TYPE: PRT
<213> ORGANISM: Rattus norvegicus

<400> SEQUENCE: 11
```

Cys Ser Leu Glu Trp Ile Gly Val Ile Asn Pro Asn Tyr Gly Thr Thr
1               5                   10                  15

Ser Tyr Cys

```
<210> SEQ ID NO 12
<211> LENGTH: 18
<212> TYPE: PRT
<213> ORGANISM: Rattus norvegicus
```

-continued

```
<400> SEQUENCE: 12

Cys Ala Arg Phe Asp Gly Tyr Tyr Gly Tyr Tyr Phe Asp Tyr Trp Gly
1               5                   10                  15

Gln Cys

<210> SEQ ID NO 13
<211> LENGTH: 16
<212> TYPE: PRT
<213> ORGANISM: Rattus norvegicus

<400> SEQUENCE: 13

Cys Arg Ala Ser Gln Asp Ile Ser Asn Tyr Leu Asn Trp Tyr Gln Cys
1               5                   10                  15

<210> SEQ ID NO 14
<211> LENGTH: 18
<212> TYPE: PRT
<213> ORGANISM: Rattus norvegicus

<400> SEQUENCE: 14

Cys Tyr Thr Ser Arg Leu His Ser Gly Val Pro Ser Arg Phe Ser Gly
1               5                   10                  15

Ser Cys

<210> SEQ ID NO 15
<211> LENGTH: 15
<212> TYPE: PRT
<213> ORGANISM: Rattus norvegicus

<400> SEQUENCE: 15

Cys Gln Gln Gly Asn Thr Leu Pro Tyr Thr Phe Gly Gly Gly Cys
1               5                   10                  15

<210> SEQ ID NO 16
<211> LENGTH: 118
<212> TYPE: PRT
<213> ORGANISM: Rattus norvegicus

<400> SEQUENCE: 16

Glu Phe Gln Leu Gln Gln Ser Gly Pro Glu Leu Val Glu Pro Gly Ala
1               5                   10                  15

Ser Val Lys Ile Ser Cys Lys His Ser Gly Tyr Ser Phe Thr Asp Tyr
                20                  25                  30

Asn Met Asn Trp Val Lys Gln Ser Asn Gly Lys Ser Leu Glu Trp Ile
            35                  40                  45

Gly Val Ile Asn Pro Asn Tyr Gly Thr Thr Ser Tyr Asn Gln Lys Phe
        50                  55                  60

Lys Gly Lys Ala Thr Leu Thr Val Asp Gln Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Phe Asp Gly Tyr Tyr Gly Tyr Tyr Phe Asp Tyr Trp Gly Gln
            100                 105                 110

Gly Thr Thr Leu Thr Val
        115

<210> SEQ ID NO 17
<211> LENGTH: 107
<212> TYPE: PRT
<213> ORGANISM: Rattus norvegicus
```

-continued

```
<400> SEQUENCE: 17

Asp Ile Val Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105
```